United States Patent [19]

Lee, Jr. et al.

[11] 3,969,821

[45] July 20, 1976

[54] ORTHODONTIC BRACKET

[76] Inventors: Henry L. Lee, Jr.; Jan A. Orlowski, both of P.O. Box 3836, South El Monte, Calif. 91733

[22] Filed: Jan. 22, 1975

[21] Appl. No.: 543,159

[52] U.S. Cl................................................ 32/14 A
[51] Int. Cl.².................................. A61C 7/00
[58] Field of Search................ 32/14 A, 1, 40 R, 71; 248/205 A

[56] References Cited
UNITED STATES PATENTS

| | | | |
|---|---|---|---|
| 3,482,809 | 12/1969 | McCall, Jr. | 248/205 A |
| 3,765,091 | 10/1973 | Northcutt | 32/14 A |

*Primary Examiner*—Robert Peshock
*Assistant Examiner*—Jack Q. Lever

[57] ABSTRACT

An orthodontic bracket is disclosed having one or more projections which extend vertically from the posterior surface of the bracket body. The projections are used for producing a glue-line having a predetermined thickness measured between the posterior surface of the bracket body and the front surface of the tooth to which the bracket is directly bonded by glueing. The thickness of the glue-line is equal to the vertical displacement of the one or more projections from the posterior surface of the bracket base. The ends of the one or more projections touch the front surface of the tooth when the bracket is directly bonded to the tooth.

A process is also disclosed for attaching the orthodontic bracket of the present invention to the tooth of a patient undergoing orthodontic treatment.

8 Claims, 5 Drawing Figures

ORTHODONTIC BRACKET

BACKGROUND OF THE INVENTION

1. Field of the Invention

Invention relates to an orthodontic bracket and process for mounting the same of the type which is directly bonded to the surface of a tooth by glueing with a dental cement. More particularly, the invention relates to an apparatus and process for directly bonding the posterior surface of the base of an orthodontic bracket to the front surface of the tooth in which a glue-line is produced having a predetermined thickness.

2. Description of the Prior Art

In recent years it has become common place to directly bond the posterior surface of the base of an orthodontic bracket to the front surface of a tooth by glueing with a dental cement. Numerous cements have been developed which have different bonding properties which necessitate the attainment of a glue-line thickness having a predetermined thickness to produce a glue joint of optimum strength. For example, one type of well known dental cement used for direct bonding orthodontic brackets requires a glue-line thickness ranging from 0.003 inches to 0.007 inches to produce the maximum strength bond. Whereas another well known dental cement produces its maximum bond strength with a glue-line thickness of 0.020 inches to 0.030 inches. Moreover, the thickness of the glue line measured between the posterior surface of the orthodontic bracket and the front surface of the tooth to which the bracket is directly bonded critically affects the magnitude of the connection forces applied to the tooth. For example, displacements of the tooth along the labial-lingual axis are normally produced by either bending the contour of the archwire to produce a force which is applied to the tooth by the bent wire or by forcing the unbent archwire into the archwire slot which has been positioned a predetermined distance from the surface of a tooth. Accordingly, it may be seen from either of the standpoints of the bond strength between the posterior surface of the orthodontic bracket and the tooth surface or from the type of orthodontic connection technique being used for straightening teeth that it has become necessary in current orthodontic practice when using the direct bonding technique to produce a glue-line having a thickness which is predetermined prior to the bonding of the bracket to the tooth surface.

In the past, the orthodontist depended largely on his own perceptive skill to directly bond the orthodontic bracket to the tooth with a glue joint having maximum strength and the proper thickness to displace the archwire slot from the archwire to insure the applying of proper correction forces. Accordingly, the attainment of a proper glue-line thickness required the expenditure of large amounts of clinical time.

Unlike the present invention, the prior art technique which depended upon the orthodontist's perceptive skills to produce a glue-line having a particular thickness did not utilize spacing elements.

U.S. Pat. No. 3,797,115 discloses an orthodontic bracket having a plurality of feet extending perpendicularly upward from the posterior surface of the bracket body which are used for retaining an adhesive which has dried prior to application of the bracket to the surface of the tooth for the final cementing of the bracket to the surface of the tooth, a fresh coating of adhesive composition is applied over the previously dried coating of cement. The bracket, including layers of dry and wet cement, is then placed directly onto the front surface of the tooth. The legs in this invention, unlike the present bracket, do not function as spacers which produce a predetermined glue-like thickness upon the cementing of the bracket body to the front surface of the tooth.

SUMMARY OF THE INVENTION

The disadvantages and limitations of the prior art as discussed above are obviated by the present invention which comprises an orthodontic bracket which is directly bonded to the surface of a tooth with a glue-line having a predetermined thickness.

The invention is an orthodontic bracket having one or more projections extending upward from the posterior surface of the base of the bracket which produce a glue-line having a predetermined thickness measured between the posterior surface of the bracket body and the tooth to which the bracket is cemented. The projections are preferably disposed near the periphery of the posterior surface of the bracket body. The one or more projections may have any one of a plurality of cross-sectional shapes. The individual projections may be scribed to indicate the displacement of the scribe marks from the posterior surface of the bracket body.

The process of the present invention comprises the method of applying the bracket described supra to the surface of a tooth.

In terms of the specification and appended claims, the terminology "predetermined glue-line thickness" defines a glue-line having a thickness which is chosen by the orthodontist prior to the initiation of direct bonding the orthodontic bracket to the tooth surface by glueing with dental cement.

DETAILED DESCRIPTION OF THE INVENTION

In each of the aforementioned views, like numerals have been used to identify like parts to facilitate the description of the present invention.

Figure 1:
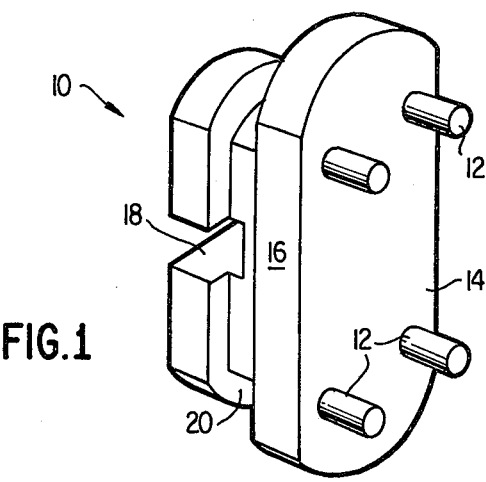
FIG. 1 is an isometic view of the present invention.
Figure 2:
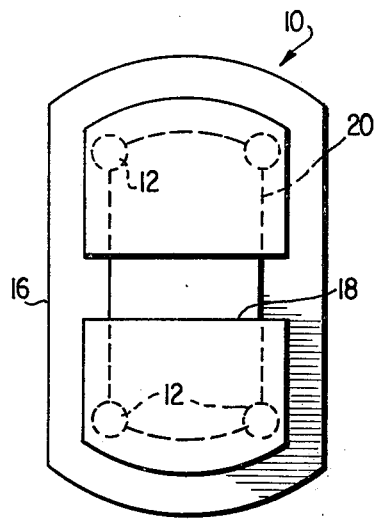
FIG. 2 is a top view of the present invention.
Figure 3:
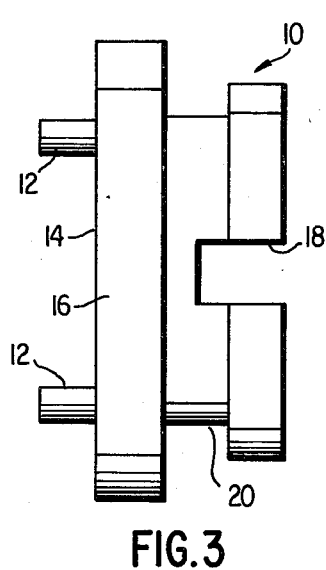
FIG. 3 is a side view of the present invention.
Figure 4:
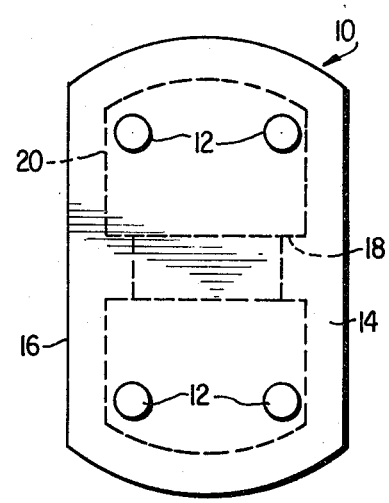
FIG. 4 is a bottom view of the present invention.
Figure 5:
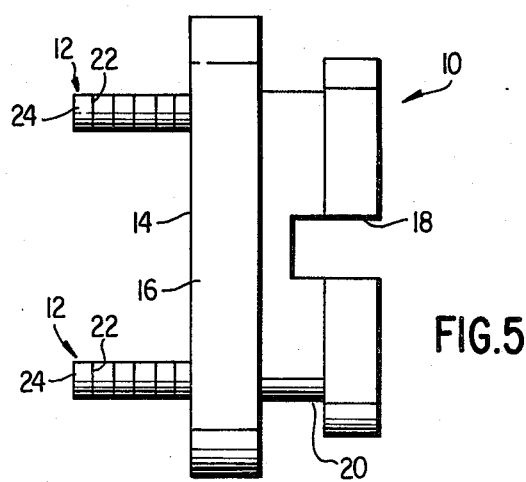
FIG. 5 is a view illustrating the projections in detail.

An orthodontic bracket 10 constructed according to the present invention consists of a plurality of projections 12 extending upward from the posterior surface 14 of the bracket body 16. While it is preferable, it is nevertheless not imperative that the projections extend perpendicularly upward from the posterior surface of the bracket base. An archwire slot 18 and a ligature undercut 20 of conventional construction are cut in the front of the bracket body 16. As is more clearly illustrated on FIG. 5, each of the projections 12 has a plurality of uniformly spaced scribed lines 22 thereon to indicate the displacement between the posterior surface 14 of the bracket body 16 and the individual scribed lines 22 on the projections. The purpose of the scribed lines 22 is to visually enable an orthodontist to determine the displacements measured from the posterior surface 14 which are less than the length of the projections 12. The orthodontist uses the scribed lines as a measure of displacement from the posterior surface 14 to abrade away any portion of the projections 12 to produce a predetermined glue-line thickness which is less than the length of the projections 12. Alternatively, different brackets may be provided having projections of various lengths.

The particular shape and number of the projections 12 is not a critical part of the invention. The shape of the cross-section area of the projections may be round, elliptical, rectangular, etc.; and they may be tapered to have the widest cross-sectional area disposed next to the posterior surface 14 of the bracket body 16 and the narrowest cross-sectional area disposed near the tip 24 of the legs 14. Moreover, the tip 24 of the individual legs may be pointed to reduce the actual area of surface contact with the front surface of the tooth to a minimum to maximize the amount of cement contacting the front surface of the tooth.

The process of attaching the bracket by direct bonding to the front surface of a tooth comprises the steps of determining the predetermined thickness of the glue-line; choosing an orthodontic bracket having one or more projections each extending vertically a distance measured from the posterior surface of the bracket which is equal to the predetermined thickness; placing a layer of glue on the posterior surface of the tooth at least as thick as the predetermined thickness; and pressing the posterior surface of the orthodontic bracket against the front surface of the tooth to produce surface contact between all the projections and the front surface of the tooth.

It should be noted that the apparatus and process of the present invention are equally applicable to orthodontic brackets constructed from either plastic or metal.

While the invention has been described in terms of a preferred embodiment, it should nevertheless be noted that numerous modifications of the invention are possible without departing from the spirit and scope of the invention. It is intended that these modifications fall within the scope of the appended claims.

What I claim as my invention is:

1. In an orthodontic bracket having a base which is adapted to be directly bonded to the front surface of a tooth by glueing and a body joined to said base, an improved orthodontic bracket comprising:
   a. a posterior surface formed on said base; and
   b. means attached to said posterior surface for producing a predetermined glue-line thickness measured between a tooth and said posterior surface when said posterior surface is directly bonded to said front surface of said tooth by glueing with a dental cement.

2. In an orthodontic bracket as recited in claim 1 wherein said means comprises:
   a. one or more projections joined to said posterior surface and extending vertically from said posterior surface.

3. In an orthodontic bracket as recited in claim 2 wherein each of said projections further comprises:
   a. an end which is adapted to touch the front surface of the tooth when said posterior surface is directly bonded to the front surface of said tooth and wherein:
   b. said glue-line thickness is equal to the length of said projections.

4. In an orthodontic bracket as recited in claim 3 wherein:
   a. said projections are joined to said posterior surface near its periphery.

5. In an orthodontic bracket as recited in claim 4 wherein:
   a. said projections are tapered with their largest cross-sectional area at the point of attachment with the posterior surface and;
   b. said projections have a point disposed at each of said ends.

6. In an orthodontic bracket as recited in claim 4 wherein:
   a. said projections have indicia of length scribed thereon to indicate the displacement between the posterior surface and the individual indicia.

7. In an orthodontic bracket as recited in claim 4 wherein said projections comprise:
   a. cylindrical sections having a conical point at said end.

8. A process for directly glueing the posterior surface of an orthodontic bracket directly to the front surface of a tooth to produce a glue-line of predetermined thickness comprising the steps:
   a. determining the predetermined thickness of the glue-line;
   b. chosing an orthodontic bracket having one or more projections each extending vertically a distance measured from the posterior surface of the bracket which is equal to the predetermined thickness;
   c. placing a layer of glue on the posterior surface of the tooth at least as thick as the predetermined thickness; and
   d. placing the posterior surface of the orthodontic bracket against the front surface of a tooth to produce surface contact between all of the projections and the front surface of the tooth.

* * * * *